United States Patent [19]

Leavitt

[11] Patent Number: 5,063,931
[45] Date of Patent: Nov. 12, 1991

[54] METHOD AND APPARATUS FOR SIGNAL DEPENDENT GAIN CONTROL

[75] Inventor: Steven C. Leavitt, Hampstead, N.H.

[73] Assignee: Hewlett-Packard Company, Palo Alto, Calif.

[21] Appl. No.: 609,312

[22] Filed: Nov. 5, 1990

[51] Int. Cl.⁵ .................................................. A61B 8/00
[52] U.S. Cl. ................................ 128/661.07; 73/900; 73/631
[58] Field of Search .................. 128/660.01, 660.06, 128/661.07; 73/602, 631, 900

[56] References Cited

U.S. PATENT DOCUMENTS

| | | | |
|---|---|---|---|
| 4,545,251 | 10/1985 | Uchida et al. | 73/900 |
| 4,688,428 | 8/1987 | Nicolas | 73/602 |
| 4,733,668 | 3/1988 | Torrence | 128/660.01 |
| 4,852,576 | 8/1989 | Inbar et al. | 128/660.06 |
| 4,930,511 | 6/1990 | Rossman et al. | 128/660.01 |

Primary Examiner—Francis Jaworski
Assistant Examiner—George Manuel
Attorney, Agent, or Firm—Frank R. Perillo

[57] ABSTRACT

A method and apparatus are provided for gain control in a Doppler or other scan system which projects a plurality of scan lines at a given angle to determine velocity of movement of a predetermined medium at the angle. A training line is generated at the angle of the scan lines, the training line being utilized to determine portions of the scan line which are in a flow medium of interest, such as blood, and portions of the scan line which are in clutter. Information from the training line is then utilized to control the gain of the scan lines so that the gain is substantially maximized when scan lines are in the flow medium, while being reduced so as not to saturate the system in general, and A/D converters in particular, when in clutter. When an image line is utilized in the system, this line may also function as the training line.

19 Claims, 2 Drawing Sheets

METHOD AND APPARATUS FOR SIGNAL DEPENDENT GAIN CONTROL

FIELD OF THE INVENTION

This invention relates to scan systems and more particularly to a method and apparatus which permits higher gains to be achieved for portions of scan lines which are in a medium of interest while not overloading the system.

BACKGROUND OF THE INVENTION

In systems such as Doppler scan systems, a plurality of scan lines are transmitted at a selected angle and echoes from these lines are processed in a known way to obtain information concerning the flow velocity of a moving medium. While such systems are used in a number of applications, the discussion to follow will be primarily in connection with ultrasonic Doppler scanners, and in particular such scanners which are being utilized for medical applications, where the Doppler effect is being utilized to determine flow velocity of blood in the heart, in a vein or artery, or in another body channel.

One problem in ultrasonic Doppler blood sampling systems is that the reflected ultrasonic signal from blood is 30 db below the signal received from the walls of the blood flow channel or other tissue through which the scan line passes. The signals received from tissue, bone, or any other material which is more reflective than blood during an ultrasonic Doppler scan may be referred to as "clutter". Since the undesired signal from such clutter is so much stronger than the desired signal from the blood, if the gain on the received signal is tuned up so as to amplify blood echoes sufficiently for the input to an analog-to-digital (A/D) converter, and in particular to obtain clear color differentiation to indicate velocity of blood flow, the input range of the A/D converters used in the system will be exceeded for the clutter (i.e. will become saturated). While this problem can be somewhat alleviated by using more expensive A/D converters having a larger input range, this may result in an unacceptable increase in system cost. More important, converters which would permit maximum gain for blood signals in some systems while not being saturated by signals from tissue are not commercially available.

A need therefore exists for a technique which permits gain to be increased for Doppler scan lines when the lines are scanning blood, with the gain being decreased when the line is scanning tissue so that optimum gain can be achieved for the blood signal without saturating the A/D converters. However, this objective is not easily accomplished since, for a given scan line, there is no easy way of predicting when the line will be in blood and when in tissue or other material.

SUMMARY OF THE INVENTION

Therefore, in accordance with the teachings of this invention, a method and apparatus are provided for controlling gain in a scan system which utilizes a plurality of lines at a given interrogate angle to determine flow velocity of a medium at such angle. Generally, a training line is utilized to determine the portions of the scan lines which are in the flow medium at the given scan angle and the portions of the scan lines which are in clutter. The information from the training line is then utilized to control the gain of all subsequent scan lines along the same interrogate angle as the training line so that the gain is substantially maximized when scan lines are in the flow medium while being reduced so as not to saturate the A/D converters when in clutter.

More particularly, the technique involves generating a training line at a given angle at which a Doppler or other flow determination is desired. In response to the training line, a signal is generated which varies with the medium through which the line is passing at selected time points along the line. The reason for the difference in signal amplitude is the difference in absorption and reflectance of the ultrasonic energy (or other scan energy) by the medium. Signals sampled at the selected time points from the training line are then converted to suitable values which are stored in a memory and the stored values are utilized for the corresponding time points to control the gain for each corresponding scan line at the given time points. For one embodiment of the invention, the variations in the received signals are variations in the signal amplitude, with values indicative of such signal amplitude being stored. The gain is then controlled inversely with signal amplitude of the training line at each time point.

For a second embodiment of the invention, the value stored is a binary value, with a first binary value being stored for time points where the training line is passing through the desired medium and a second binary value being stored for time points where the training line is not passing through such medium. The gain is then controlled to cause a higher gain for time points having the first binary value than for time points having the second binary value. A threshold value may be established with the first binary value being stored when signal amplitude is below the selected threshold and second binary values being stored when the amplitude is above the selected threshold. For the preferred embodiment, the analog signal amplitude values are converted to digital values which are stored and the stored digital values are then converted back to analog values for gain control.

The foregoing and other objects, features and advantages of the invention will be apparent from the following more particular description of preferred embodiments of the invention as illustrated in the accompanying drawings.

IN THE DRAWINGS

DETAILED DESCRIPTION

In an ultrasonic scanning system having Doppler color flow capabilities, a single ultrasonic line is projected at a given angle in order to permit a two dimensional image of the scanned area to be generated on, for example, a cathode ray tube screen. For areas where Doppler color flow images are desired, which images indicate the direction of blood flow at the scanned point by color (the image, for example, being blue with blood flowing in one direction and red for blood flowing in the opposite direction) and indicate magnitude of the velocity by color intensity or hue, a plurality of additional lines, for example, eight lines, are projected at the same angle. These eight lines are processed to obtain the information necessary to generate the color flow image along that particular scan angle. An example of a color flow Doppler ultrasonic scanning system which operates generally as indicated above is the Hewlett-Packard Model HP SONOS 1000.

As previously indicated, one problem with systems of this type is that blood tends to reflect ultrasonic signals much weaker than does tissue. The typically 30 db difference in the reflected signal can sometimes result in weak signals being obtained from the areas of most concern, and thus in the blood flow images not being as clearly differentiated as possible.

Figure 1:
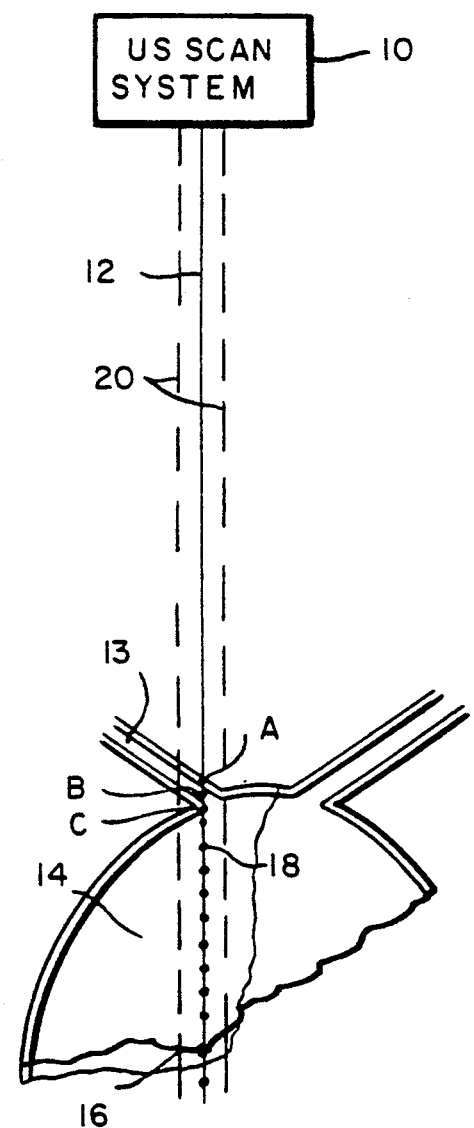
FIG. 1 is a diagram illustrating the environment in which the teachings of this invention might be utilized.

FIG. 1 illustrates an environment in which the method and apparatus of this invention might be utilized. In this environment, an ultrasonic scanning system 10 generates an ultrasonic beam 12 at a selected angle which passes through an area of the body which is to be imaged In this case, the beam is passing through an artery 13, a chamber 14 of the heart, and a heart valve 16. There are a plurality of time points 18 on beam 12. Points 18 are points at which the beam 12 arrives at successive time intervals along its path of travel.

In addition to the image beam 12, in areas where color flow information is required, system 10 also projects a plurality of Doppler beams or lines 20 at the same angle as the beam 12. In a typical system, there would be eight separate Doppler lines projected being coincident along beam 12. While in FIG. 1, for purposes of permitting visibility, the lines 12 and 20 are shown as being spatially separated, these lines are in practice projected along substantially the same path at successive time intervals.

As can be seen from FIG. 1, the beams 12 and 20 pass through the walls of artery 13 as well as the blood flowing therethrough, through the walls of chamber 14 and through other tissue not shown in the figure. Thus, at time point A, line 12 is in tissue while at time point B, it is in blood. At time point C, the line is again in tissue while at the succeeding time points, it is in chamber 14 where it may be in either blood or tissue depending on the part of the chamber where it is located. As previously indicated, the amplitude of the signal returned to system 10 varies depending on the medium through which an ultrasonic scan line is passing at a particular time point.

In accordance with the teachings of this invention, either the image line 12 or a separately generated training line, if image line 12 is not available or is otherwise not useable as a training line, is used as a training line to determine the medium through which a beam projecting at the angle of the training beam is passing at successive time points. This information is then stored and used to control gain for all subsequent Doppler lines 20 at the same angle so that these gains may be optimized in regions such as time point B where the beam is passing through blood. The gain profile for all subsequent lines after the training line would be substantially the same.

Figure 2:
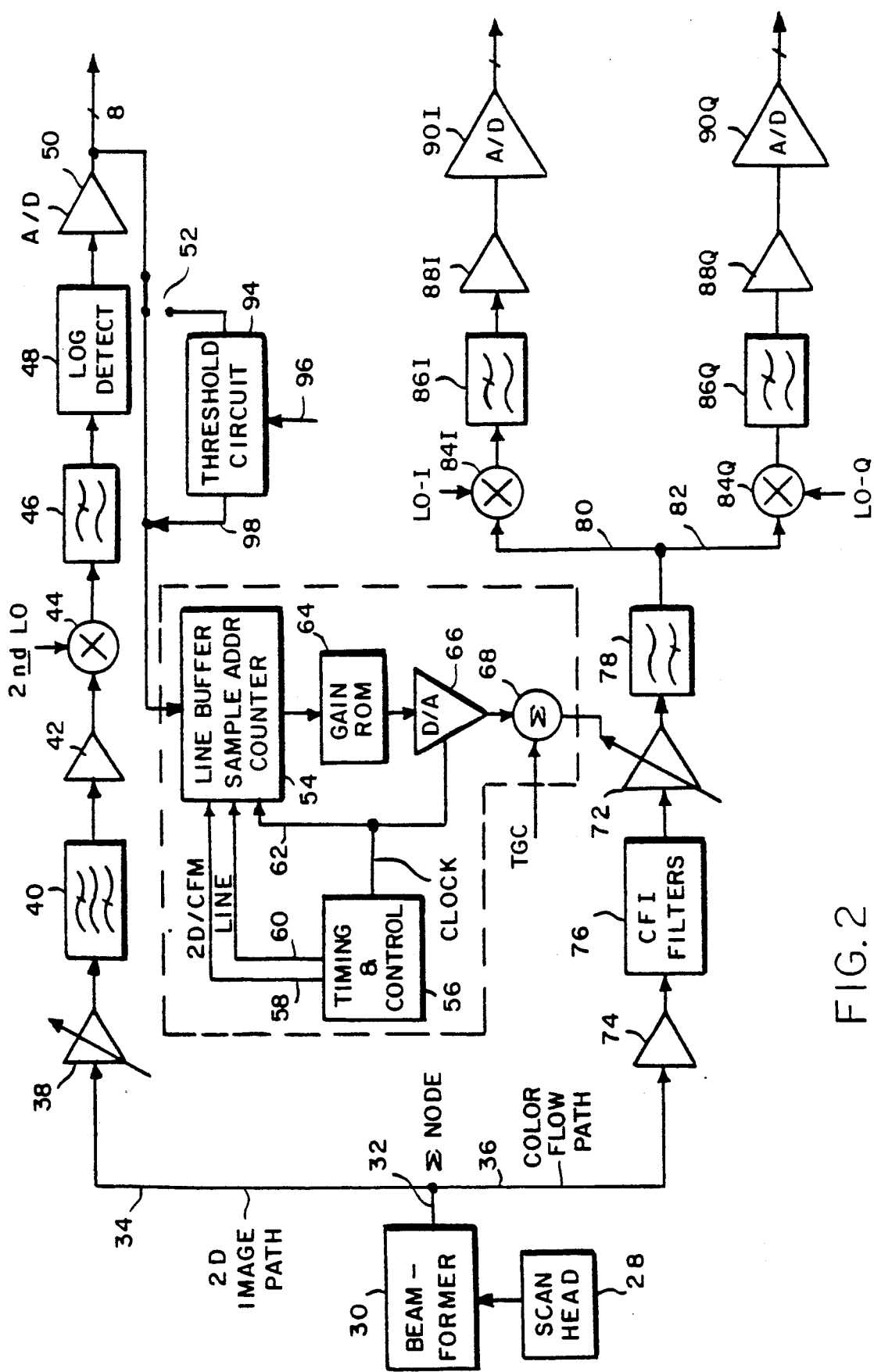
FIG. 2 is a schematic circuit diagram of circuitry incorporating the teachings of this invention for processing the image and color flow signals received in an ultrasonic scanning system.

FIG. 2 shows a circuit for use in the system 10 for accomplishing this gain control function. In FIG. 2, the echo signal received from scan head 28 at each time point along a scan line is processed by a suitable beam forming circuit 30 to provide a signal on line 32 which varies as a function of the received echo. The signal on line 32 is passed through a first path 34 if the line is an image line 12 and through a second path 36 if the line resulting in the echo signal is a color flow line 20. Path 34 would also be utilized for a line which served solely as a training line without having any image function. However, it is preferable that an image line be used as the training line since a special line would penalize the scanning frequency of the system. Since the ultrasonic signal which results in the echo is known, suitable gating (not shown) can be provided to direct a signal on line 32 to the appropriate path.

Assuming the initial line is an image line the RF analog signal on line 34 would be passed through a series of circuits commonly employed in systems of this type, which circuits do not specifically form part of this invention. These circuits include a time gain compensation (TGC) circuit 38 which maintains a uniform gain for the signal for time points 18 located at successively greater distances from system 10, bandpass filter 40, amplifier 42, mixer 44, low pass filter 46 and log detect circuit 48 which converts the linear analog input& signal to a logrithmic output signal.

The output from circuit 48 is applied to A/D converter 50. For one embodiment of the invention, the digital output from converter 50, which is applied to a scan converter circuit to control image display, is also applied through switch 52 in the normally closed position shown in the figure to line buffer/sample address counter 54. The data applied to buffer 54 is clocked to appropriate addresses therein under control of signals from timing and control circuit 56. Circuit 56 generates an output on line 58 which indicates whether the information being received on line 32 is color flow or image information, image information being stored in the buffer 54 and information being read out of the buffer when color flow information is received. A signal appears on line 60 when signal for a line is first received to synchronize the sample address counter. Clock signals appear on line 62. Values are thus stored in buffer 54 for each time point under control of the signals on lines 58-62. There might typically be 400 time points sampled on a given training line. When all echoes from training or image line 12 have been received, buffer 54 contains a sequence of values which are indicative of signal amplitude for the training line at a sequence of selected time points along the line. As previously indicated, these amplitudes will be substantially greater for time points which are in tissue than for time points which are blood.

When a color flow line is being generated, the signal on line 58 indicates this, causing buffer 54 to read out the value stored for each time point in synchronism with the color flow line reaching the corresponding time point. The outputs from buffer 54 are applied as address inputs to gain ROM 64, ROM 64 containing an appropriate digital value for each time point value input, which digital value is read out in response to the address input from buffer 54. As, for example, time point A is reached for a color flow line 20, the value stored in buffer 54 for line 12 for this time point is read out to address gain ROM 64. The addressed location contains a predetermined gain value for input to D/A converter 66. Converter 66 is also clocked by signals on line 62 to generate an analog output which corresponds to, but does not necessarily equal, the analog signal for that time point for line 12.

The analog output signal from converter 66 is applied to a summing circuit 68 where it is summed with a time gain control signal 70 so that the output from circuit 68 is corrected to account for attenuation due to depth of sample. The output from circuit 68 is provided as a control input to a variable gain amplifier 72. The values from ROM 64 and D/A converter 66 are selected such that the output of amplifer 72 for a time point varies inversely with the value stored in buffer 54 for such time point. The information input &:o amplifier 72 is a color flow echo signal which has been previously passed through standard amplifier circuit 7 and color flow filter circuits 76. The output from amplifier 72 is passed through standard filtering circuits 78 to both a real path 80 and an imaginary path 82. Each path contains a mixer 84, filter 86 amplifier 88 and A/D converter 90. These elements are all standard.

Thus, if during the image or training line 12 it is determined that, for a particular time point 18, the line is passing through blood, resulting in a signal having a relatively lower level being stored in buffer memory 54 for such time point, the value stored in ROM 64 for such signal can be selected and amplifier 72 can be adjusted, such that the amplifier gain causes the output for color flow lines at that time point to be of an amplitude close to the maximum capacity of converters 90. However, if it is determined from the training or image line for a particular time point that for a scan line at the given angle, such time point is in tissue, resulting in a higher level signal output being stored in buffer 54 for such time point, the resulting ROM output for such time point will control amplifier 72 to reduce or maintain the signal level at its output low enough so that the output for color flow lines at such time point does not saturate converters 90.

A relatively simple method and apparatus is thus provided which optimizes the signal level for color flow lines when the lines are passing through blood or other media of interest while not overloading the system, and in particular A/D converters 90, when such lines are passing through clutter.

FIG. 2 also illustrates an alternative embodiment of the invention which comes into play when switch 52 is transferred from the position shown in FIG. 2 to its alternative position. Under these circumstances, the output from converter 50 is passed through threshold circuit 94 before being applied to buffer 54. The threshold for circuit 94 may be controlled by a signal on line 96. Threshold circuit 94 receives the multibit, for example eight bit, signal values from converter 50 and generates a one bit output on line 98. This value may, for example, be a "1" if the input is below a predetermined threshold, indicating that the training line for the given time point is in blood, and a "0" if the input is above the threshold. The threshold value selected will depend on various parameters of the system utilized, and may either be preset for a given system, may be adjustable for the system based on certain criteria, or may be empirically determined.

The binary output from circuit 94 is applied to line buffer 54 and is stored in an address location in the buffer for the time point. This process is the same as that described for the previous embodiment of the invention, except that a single bit is stored rather than, for example, eight bits.

On readout, the single bit is applied to gain ROM 64, resulting in a predetermined digital input to converter 66. The resulting analog control signal causes, for example, a higher gain from amplifier 72 if a 1 is present and a lower gain if a 0 is present. The manner in which the outputs from the gain ROM 64 and converter 66 are utilized to control gain at each time point for color flow lines for this embodiment of the invention is the same as that decribed for the previous embodiment of the invention.

While in FIG. 2 a switch 52 has been provided to permit the circuit to either operate with quasi-continuous control of gain or in a binary mode with a first gain for time points in blood and a second lower gain for time points in tissue, a system would normally operate in a variable gain or binary mode, and not provide an option to operate in either mode. Also, while in FIG. 2 a summer 68 is provided to perform the time gain control function, this function could also be provided by ROM 64, with summer 68 being eliminated. For such embodiment, TGC line 70 would be an additional addressing input to ROM 64, there being a plurality of different ROM outputs provided for each potential ROM input from buffer 54. Another option would be to have the TGC function performed at amplifier 74.

Further, while the discussion above has been with reference to a Doppler ultrasonic medical scanning system, and in particular to a system having the various components shown in FIG. 2, these are not limitations on the invention. The invention could thus be utilized with any system which employs Doppler, or other lines to do velocity indications, where the reflections from the medium of interest are less than those from surrounding medium. In particular, the system could be utilized in other ultrasonic Doppler systems than that shown in the figure.

Thus, while the invention has been particularly shown and described above with reference to preferred embodiments, the foregoing and other changes in form and detail may be made therein by one skilled in the art without departing from the spirit and scope of the invention.

What is claimed is:

1. A gain control circuit for use in a system which generates a plurality of scan lines at a given angle said line passing through at least one medium to determine velocity of movement of a predetermined one of the mediums at said angle, the circuit comprising;
   means for generating a training line at said given angle and for receiving echo signals in response thereto;
   means responsive to received echo signals from the training line for generating a signal which varies with the medium through which the training line is passed at selected time points along the line;
   means responsive to the generated signal at said selected time points for storing selected values; and
   means for utilizing the value stored for a given one of said selected time points to control the gain for each scan line at the given angle for the given one of the selected time points.

2. A circuit as claimed in claim 1 wherein said signal variations are variations in signal amplitude, values indicative of said signal amplitude being stored; and
   wherein the gain control means controls gain for the given time point inversely with the signal amplitude of the training line at the time point.

3. A circuit as claimed in claim 2 wherein the value stored is proportional to signal amplitude, gain for the scan lines for the given time point varying inversely with the stored value for the time point.

4. A circuit as claimed in claim 2 wherein the value stored is a binary value, being a first binary value for time points where the training line is passing through the predetermined medium and a second binary value for time points where the training line is not passing through the predetermined medium.

5. A circuit as claimed in claim 4 wherein said gain control means causes a higher gain for time points having said first binary value than for time periods having said second binary value.

6. A circuit as claimed in claim 4 including threshold means for generating said first binary value when the signal amplitude is below a selected threshold value for a given time period, and generating said second binary value when the amplitude is above the selected threshold value.

7. A circuit as claimed in claim 2 wherein said signal generating means includes means for converting said signal amplitude at the selected time points to digital values, and means for storing said digital values.

8. A circuit as claimed in claim 7 wherein said means for utilizing includes mean for converting the stored digital values to analog values for gain control.

9. A circuit as claimed in claim 1 wherein said system is an ultrasonic Doppler scan medical system, and wherein said predetermined medium is blood.

10. A circuit as claimed in 9 wherein said system projects an image line at the given angle in addition to the scan lines, and wherein the image line also functions as said training line.

11. A method to control gain in a system which generates a plurality of scan lines at a given angle, said line passing through at least one medium to determine velocity of movement of a predetermined one of the mediums at said angle, the method comprising the steps of;
generating a training line at said given angle;
generating a signal in response to echo signals received from the training line which generated signal varies with the medium through which the training line is passing at selected time points along the line;
storing selected values in response to the generated signal at said selected time points; and
utilizing the stored value for a given one of the selected time points to control the gain for each scan line at the given angle for the given time point.

12. A method as claimed in claim 11 wherein said signal variations are variations in signal amplitude, values indicative of said signal amplitude being stored; and
wherein the gain control step controls gain for the given time point inversely proportional with the signal amplitude of the training line at the time point.

13. A method as claimed in claim 12 wherein the value stored is a binary value, being a first binary value for time points where the training line is passing through the predetermined medium and a second binary value for time points where the training line is not passing through the predetermined medium.

14. A method as claimed in claim 13 wherein said gain control step includes the steps of causing a higher gain for time points having said first binary value than for time periods having said second binary value.

15. A method as claimed in claim 13 including the step of generating said first binary value when the signal amplitude is below a selected threshold value for a given time period, and generating said second binary value when the amplitude is above the selected threshold value.

16. A method as claimed in claim 12 wherein said signal generating step includes the step of converting said signal amplitude at the selected time points to digital values, said storing step storing said digital values.

17. A method as claimed in claim 16 wherein said utilizing step includes the step of converting the stored digital values to analog values.

18. A method as claimed in claim 11 wherein said system is an ultrasonic Doppler medical scanning system, and wherein said predetermined medium is blood.

19. A method as claimed in claim 19 wherein said system projects an image line at the given angle in addition to the Doppler scan lines, and wherein the image line also functions as said training line.

* * * * *